United States Patent [19]
Hideshima

[11] Patent Number: 4,799,489
[45] Date of Patent: Jan. 24, 1989

[54] TONOMETER

[75] Inventor: Masayuki Hideshima, Tokyo, Japan

[73] Assignee: Tokyo Kogaku Kikai Kabushiki Kaisha, Tokyo, Japan

[21] Appl. No.: 124,835

[22] Filed: Nov. 24, 1987

[30] Foreign Application Priority Data

Nov. 27, 1986 [JP] Japan ................................ 61-282476

[51] Int. Cl.[4] ................................................ A61B 3/16
[52] U.S. Cl. ...................................................... 128/648
[58] Field of Search ................................ 128/648, 645

[56] References Cited

U.S. PATENT DOCUMENTS 3,538,754 11/1970 Grolman et al. .................... 128/648
3,572,100 3/1971 Grolman et al. .................... 128/648
3,585,849 6/1971 Grolman ............................ 128/642
3,832,890 9/1974 Grolman et al. .................... 128/648

OTHER PUBLICATIONS

Curric et al, "The Use of Telemtory to Study . . . ", Intl. Symp. Biotelemetry, Nijnmenen, Neth. May 8, 1971, p. 3281.

*Primary Examiner*—Edward M. Coven
*Attorney, Agent, or Firm*—Finnegan, Henderson, Farabow, Garrett & Dunner

[57] ABSTRACT

A tonometer comprising an eye pressure measuring device including a fluid discharge device for discharging a fluid toward an eye to be tested, a pulse wave phase detecting device for detecting a phase cycle of pulse wave due to pulse fluctuation of the eye to be tested, a pulse wave phase area establishing device for establising whether or not an eye pressure measurement was carried out in any phase area of the pulse wave, according to an output pulse caused by a fluid discharge during the eye pressure measurement and an output of the pulse wave phase detecting device, and a recognizing device for recognizing a measured eye pressure value corresponding to a phase area of the eye pressure measuring time according to the output of the pulse wave phase area establishing device.

6 Claims, 7 Drawing Sheets

FIG. 3

ROM 16

| UNDER BIT \ UPPER BIT | 0 | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| 0 | | | | | | | | | | | | | | | | |
| 1 | | | | | | | | | | | | | | | | |
| 2 | | | | | | | | | | | | | | | | |
| 3 | 1 | 2 | 3 | 4 | | | | | | | | | | | | |
| 4 | 1 | 1 | 2 | 3 | 4 | | | | | | | | | | | |
| 5 | 1 | 1 | 2 | 3 | 3 | 4 | | | | | | | | | | |
| 6 | 1 | 1 | 2 | 2 | 3 | 3 | 4 | | | | | | | | | |
| 7 | 1 | 1 | 2 | 2 | 3 | 3 | 4 | 4 | | | | | | | | |
| 8 | 1 | 1 | 2 | 2 | 3 | 3 | 4 | 4 | 4 | | | | | | | |
| 9 | 1 | 1 | 2 | 2 | 3 | 3 | 3 | 4 | 4 | 4 | | | | | | |
| 10 | 1 | 1 | 2 | 2 | 2 | 3 | 3 | 3 | 4 | 4 | 4 | | | | | |
| 11 | 1 | 1 | 1 | 2 | 2 | 2 | 3 | 3 | 3 | 4 | 4 | 4 | | | | |
| 12 | 1 | 1 | 1 | 2 | 2 | 2 | 3 | 3 | 3 | 4 | 4 | 4 | 4 | | | |
| 13 | 1 | 1 | 1 | 2 | 2 | 2 | 2 | 3 | 3 | 3 | 4 | 4 | 4 | 4 | | |
| 14 | 1 | 1 | 1 | 2 | 2 | 2 | 2 | 3 | 3 | 3 | 3 | 4 | 4 | 4 | 4 | |
| 15 | 1 | 1 | 1 | 1 | 2 | 3 | 2 | 2 | 3 | 3 | 3 | 3 | 4 | 4 | 4 | 4 |

FIG. 4
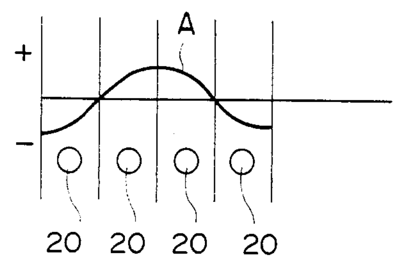
FIG. 5
| 8 | 4 | 2 | 1 |
|---|---|---|---|
| $2^3$ | $2^2$ | $2^1$ | $2^0$ |
| 0 | 0 | 0 | 1 |
| 0 | 0 | 1 | 0 |
| 0 | 1 | 0 | 0 |
| 1 | 0 | 0 | 0 |
FIG. 7
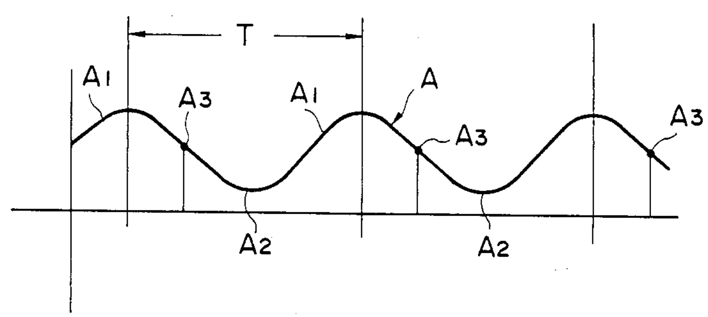

TONOMETER

BACKGROUND OF THE INVENTION

1. Field of the Invention

This invention relates to an improvement of a tonometer, in which the reliability on a result of eye pressure measurement is much improved while taking into consideration the eye pressure fluctuation due to pulse fluctuation.

2. Related Art of the Invention

As a conventional tonometer, there is known a noncontact type tonometer, e.g., air puff type tonometer, in which a fluid pulse is discharged toward an eye of a subject to be tested and the pressure value of the eye to be tested is measured based on a corneal applanation of the eye. In this type of a tonometer, an air pulse as the fluid pulse is momentarily discharged towards the eye to be tested in such a short time as several tens ms for example and the cornea is flattened or applanated in such a short time as several tens ms to carry out an eye pressure measurement. In this case, however, there is present the following inconvenience. That is, the pressure of the eye to be tested changes corresponding to the pulse fluctuation. It is said that the eye pressure fluctuation is several mmHg maximum. While the eye pressure value of a normal eye is normally 10 mmHg to 20 mmHg, his pulse fluctuation is normally 60 to 120 times per minute. The cycle T (see FIG. 7) of a pulse wave A of the pulse fluctuation is approximately 500 ms at the shortest. Therefore, if the eye pressure is measured without taking into consideration the eye pressure fluctuation due to pulse fluctuation, the measured value itself becomes dubious. The reason is that if the eye pressure measurment is carried out at the top $A_1$ of the pulse wave A as shown in FIG. 7, the eye pressure value obtained becomes higher corresponiding thereto, while if the eye pressure measurement is carried out in the bottom $A_2$ of the pulse wave A, the eye pressure value obtained becomes lower corresponding thereto.

To overcome this inconvenience, there is proposed a tonometer for measuring an eye pressure taking into consideration the eye pressure fluctuation due to pulse fluctuation (U.S. Pat. No. 3,572,100). In the tonometer disclosed in this U.S. Pat. No. 3,572,100, an eye pressure measurement is carried out in synchronism with the same phase place $A_3$ of the pulse wave A due to pulse fluctuation. According to this tonometer, errors of measurement due to pulse fluctuation can be removed.

In general, it is required for a noncontact type tonometer to ensure a strict alignment with respect to an eye to be tested. In order to carry out the eye pressure measurement correctly, such a strict alignment accuracy is required as a zero point something mm or less. Therefore, in the tonometer disclosed in the U.S. Pat. No. 3,572,100, since the eye pressure measurement is carried out in synchronism with the same phase place $A_3$ of the pulse wave A due to pulse fluctuation 1 to 2 times per second, the aligning state of the tonometer must be maintained for approximately 1 second maximum with respect to the eye to be tested. However, since the eye to be tested repeats a fixation flick or tremor at the cycle of 0.2 to 3 seconds within the range of from zero point something mm to 1 mm, it is difficult to maintain the aligning state for 1 second. Therefore, the inspector or examiner needs a long experience. In addition, the operation of this type of conventional tonometer is troublesome.

SUMMARY OF THE INVENTION

It is therefore an object of the present invention to provide a tonometer which is capable of correctly measuring an eye pressure without receiving an adverse affection from pulse fluctuation.

Another object of the present invention is to provide a tonometer, in which a correct eye pressure can be displayed on a display means.

A further object of the present invention is to provide a tonometer, in which a correct eye pressure can be measured by obtaining the phase of pulse wave during the eye pressure measuring time from a memory means for memorizing a phase area information of the pulse wave.

The feature of the present invention is present in that a tonometer is provided with a means for establishing a pulse wave phase area to establish whether or not the eye pressure measurement was carried out in any phase area of the pulse wave so as to recognize the phase area during the eye pressure measuring time.

Another feature of the present invention is present in that a phase of pulse was during the measuring time is obtained from a memory means for memorizing a phase area information of the pulse wave, thereby to obtain a correct measurement of eye pressure.

BRIEF DESCRIPTION OF THE DRAWINGS

FIG. 3 is an illustration for explaining the information memorized in ROM of FIG. 1;

FIG. 4 is a schematic view for explaining one example of a display circuit of FIG. 1;

FIG. 5 is a table showing binary to decimal values used for explaining the one example of the display circuit of FIG. 4;

FIG. 7 is a schematic view for explaining the problems involved in the conventional tonometer.

DETAILED DESCRIPTION OF THE EMBODIMENT

Figure 1A:
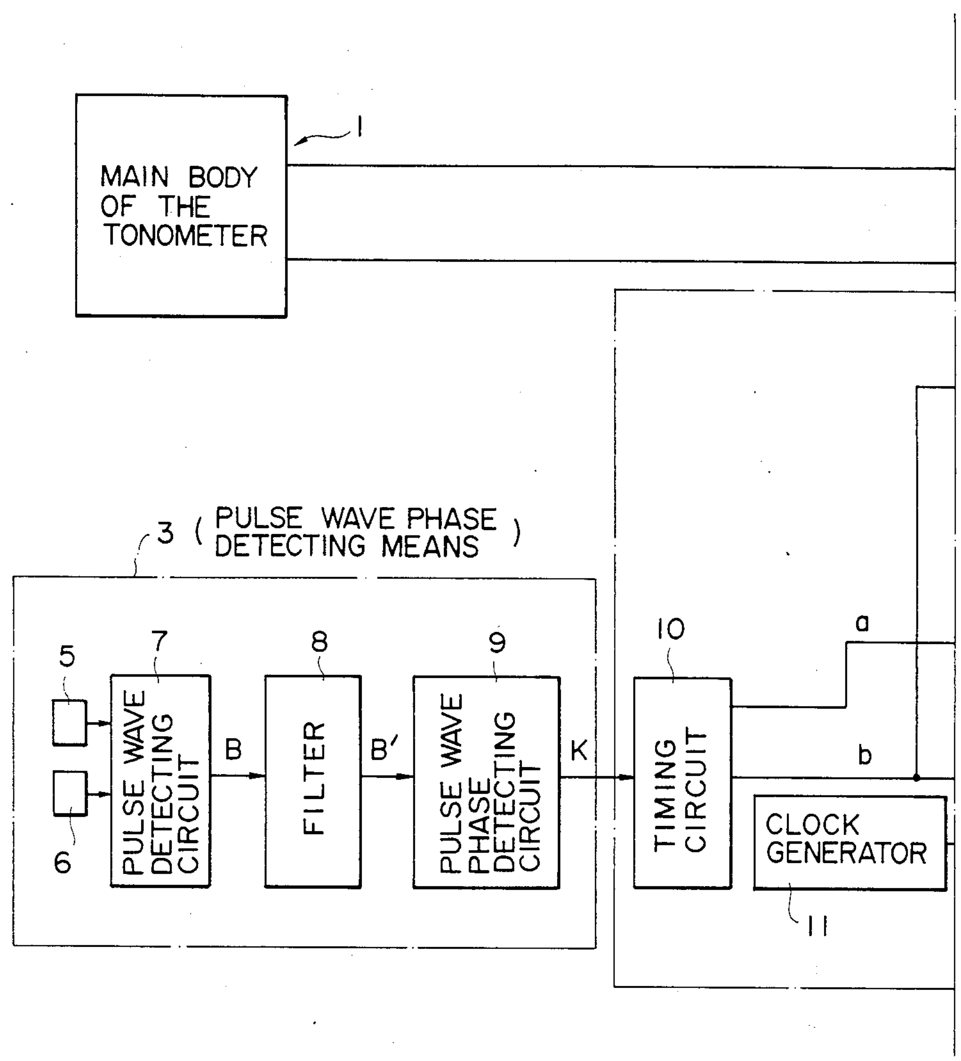
FIG. 1A and FIG. 1B taken together as in FIG. 1, are illustrations of a circuit diagram showing an important portion of a tonometer according to the present invention.
Figure 1:
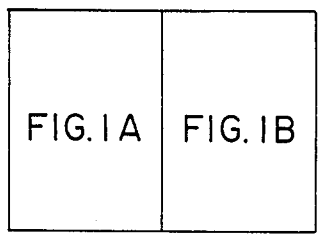
Figure 1B:
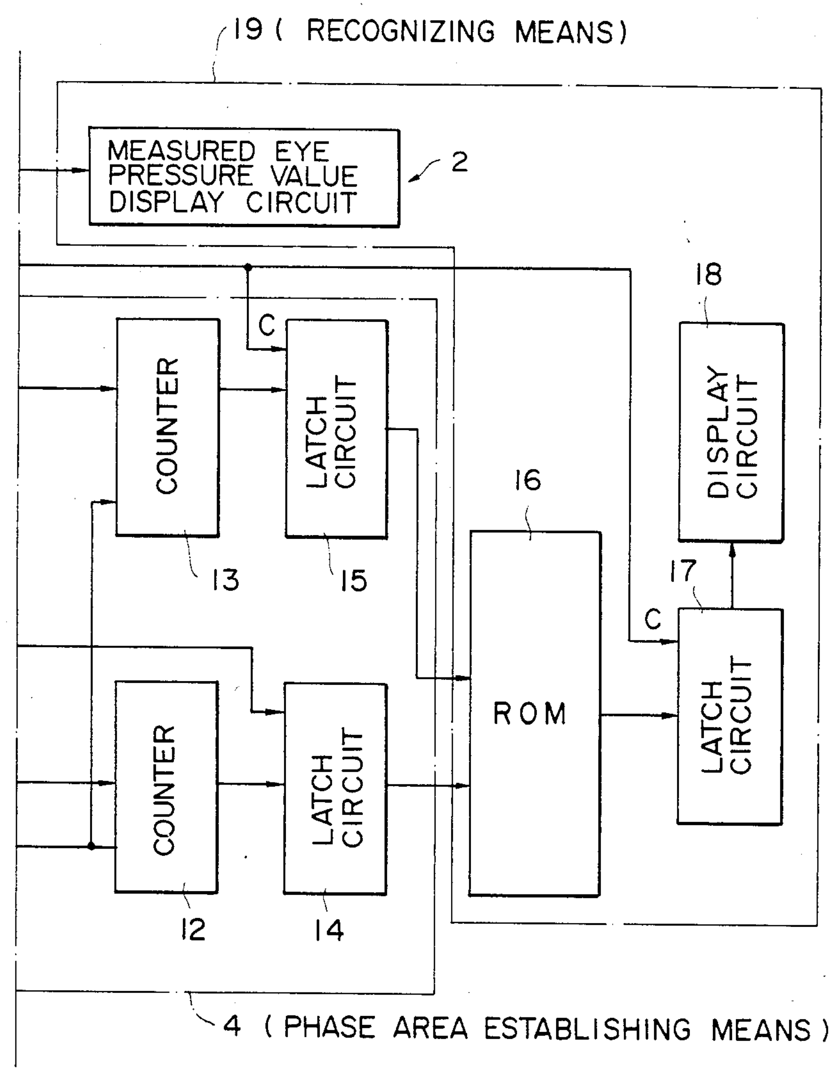

FIGS. 1A and 1B illustrate a first embodiment of a noncontact type tonometer according to the present invention. In FIGS. 1A and 1B, reference numeral 1 denotes a main body of the tonometer, 2 a means for displaying a measured eye pressure, 3 a means for detecting a pulse wave phase, and 4 a means for establishing a pulse wave area. The tonometer main body 1 includes a means (not shown) for discharging an air pulse and an eye pressure measuring circuit (not shown). The air pulse discharging means and eye pressure measuring circuit used in this embodiment are known in U.S. Pat. No. 3,585,849 or disclosed in U.S. patent application Ser. No. 743,417 filed on June 11, 1985.

Figure 2:
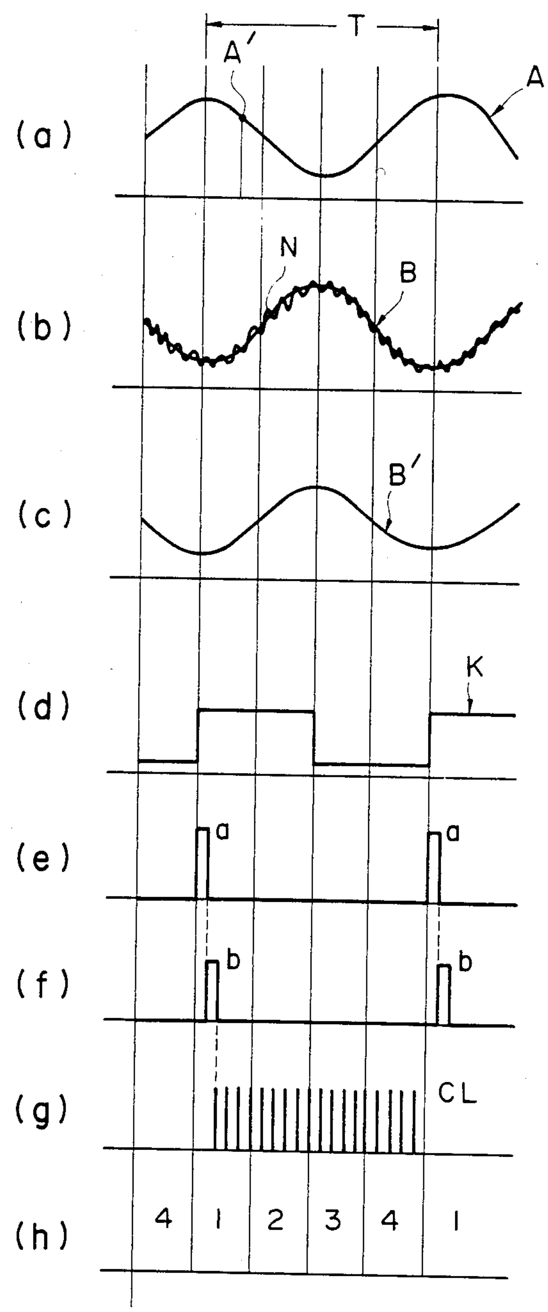
FIG. 2 is a timing chart for explaining the function of the circuit of FIG. 1.

The pulse wave phase detecting means 3 has such a function as to detect the phase cycle of the pulse wave A (see FIG. 2(*a*)) due to pulse fluctuation of the subject to be tested. The pulse wave phase detecting means 3 has electrodes 5 and 6. The electrodes 5 and 6 are connected with a filter 8 through a pulse wave detecting circuit 7 respectively, while the filter 8 is connected with a pulse wave phase detecting circuit 9. If the finger touches the electrodes 5 and 6, the electric resistance is changed between the respective skins touching the electrodes 5 and 6 due to change of blood flow caused by pulse fluctuation. As a result, a pulse wave signal B shown in FIG. 2(*b*) is taken out of the pulse wave detecting circuit 7.

The filter 8 has such a function as to remove a noise composition included in the pulse wave signal B. The pulse wave phase detecting circuit 9 contains a pulse wave signal B' (see FIG. 2(*c*)) from which the noise N has been removed. The pulse wave phase detecting circuit 9 is adapted to generate a rectangular wave K (see FIG. 2(*d*)) in response to the pulse wave signal B'. The phase (cycle T) of the pulse wave A is established by the rectangular wave K.

The rectangular wave K is input into the phase area establishing means 4. The phase area establishing means 4 has such a function as to establish whether or not the eye pressure measurement was carried out in any phase area of the pulse wave A according to an output pulse based on the fluid discharge at the time when the eye pressure is measured and the output of the pulse wave phase detecting means 3. The phase area establishing means 4 comprises a timing circuit 10, a clock generator 11, counters 12 and 13, and latch circuits 14 and 15. The timing circuit 10 has such a function as to output a latch signal a (see FIG. 2 (*e*)) and a reset signal b (see FIG. 2 (*f*)) in response to the rectangular wave K. The reset signal b is output immediately after the latch signal a is output. The reset signal b and a clock pulse CL of the clock generator 11 are input into the counters 12 and 13. The counters 12 and 13 have such a function as to count the number of clock pulse CL (see FIG. 2 (*g*)), and the counting content is cleared by the reset signal b.

The latch signal a and the count output of the counter 12 is input into the latch circuit 14. The latch circuit 14 is adapted to latch the counting content of the clock pulse CL which is input during the cycle T of the pulse wave. Provided that the time interval of the generation of the clock pulse CL is, for example, 100 ms and that 10 clock pulses CL are counted, the cycle T of the pulse wave A is 1 second. A latch signal c and the count output of the counter 13 are input into the latch circuit 15. The latch signal c is output from the tonometer main body 1 at the time when the fluid is discharged. The latch circuit 15 is adapted to latch the counting content of the clock pulse CL which is input thereto before the latch signal c is input. The value of the counting content of the clock pulse CL latched in the circuit 5 is smaller than the value of the counting content which the latch circuit 14 has latched. The reason is that the eye pressure measurement is carried out in any phase place A' (see FIG. 2 (*a*)) within the range of the cycle T of the pulse wave A.

The latch circuits 14 and 15 are adapted to output the counting content as an address signal to a ROM 16. In this ROM 16, an address is designated using 8 bits. The latch circuit 14 has such a function as to designate 4 bits in the high-order digit, while the latch circuit 15 has such a function as to designate 4 bits in the low-order digit. The 4 bits in the high-order digit corresponds to the number of the clock pulse CL during the tye pressure measuring time, while the 4 bits in the low-order digit corresponds to the number of the cycle T of the pulse wave A. This ROM 16 memorizes a phase area information obtained by dividing the phase of the pulse wave A. In this embodiment, the phase of the pulse wave (FIG. 2 (h)) is divided into four equal parts, and the ROM 16 memorizes a phase area information, i.e., an information regarding that when the 4 bits in the low-order digit is established with respect to the 4 bits in the high-order digit, the 4 bits in the low-order digit belongs to which part of the division of the four equal parts, wherein [1] corresponds to the first ¼ cycle of the pulse wave A, [2] corresponds to the first 2/4 cycle, [3] corresponds to the first ¾ cycle, and [4] corresponds to the last 4/4 cycle. If an information corresponding to a phase area is memorized in the ROM 16 as shown in FIG. 3, it can be established whether or not the eye pressure measurement was carried out in any phase area by corresponding it to the cycle T of the pulse wave A per each subject to be tested. In FIG. 3, the number of the clock pulse CL corresponding to the 4 bits in the low-order digit and the 4 bits in the high-order digit are displayed in decimal number.

The ROM 16 is adapted to output an information corresponding to the phase where the eye pressure measurement was carried out according to the address signals from the latch circuits 14 and 15, to the latch circuit 17. The latch circuit 17 is adapted to latch an information corresponding to the phase area where the eye pressure measurement was carried out according to the latch signal c and the phase area during the eye pressure measuring time is displayed in the display circuit 18 according to the output from the latch circuit 17. The ROM 16, latch circuit 17, and display circuit 18, together with the measured eye pressure value display circuit 2, constitute a recognizing means 19 for recognizing a measured eye pressure value corresponding to the phase area during the eye pressure measuring time according to the output of the pulse wave phase area establishing means 4. Therefore, the examiner is able to know the phase area of the pulse wave A where the eye pressure measurement was carried out based on the display of the display circuit 18. As a result, he is able to recognize a measured eye pressure value corresponding to the phase area during the eye pressure measuring time.

Supposing that the display circuit 18 is provided with four pieces of LED 20 in such a manner as to correspond to the respective phase areas of the pulse wave A as shown in FIG. 4, to display the phase area during the eye pressure measuring time. If the phase area [1] is set in such a manner as to correspond to the numeric value [1], the phase area [2] to the numeric value [2], the phase area [3] to the numeric value [4], and the phase area [4] to the numeric value [8], and if these numeric values are memorized in the ROM 16 as binary information, the display of the phase area is made conveniently because 1 bit can be corresponded to each LED 20 as shown in FIG. 5.

Figure 6A:
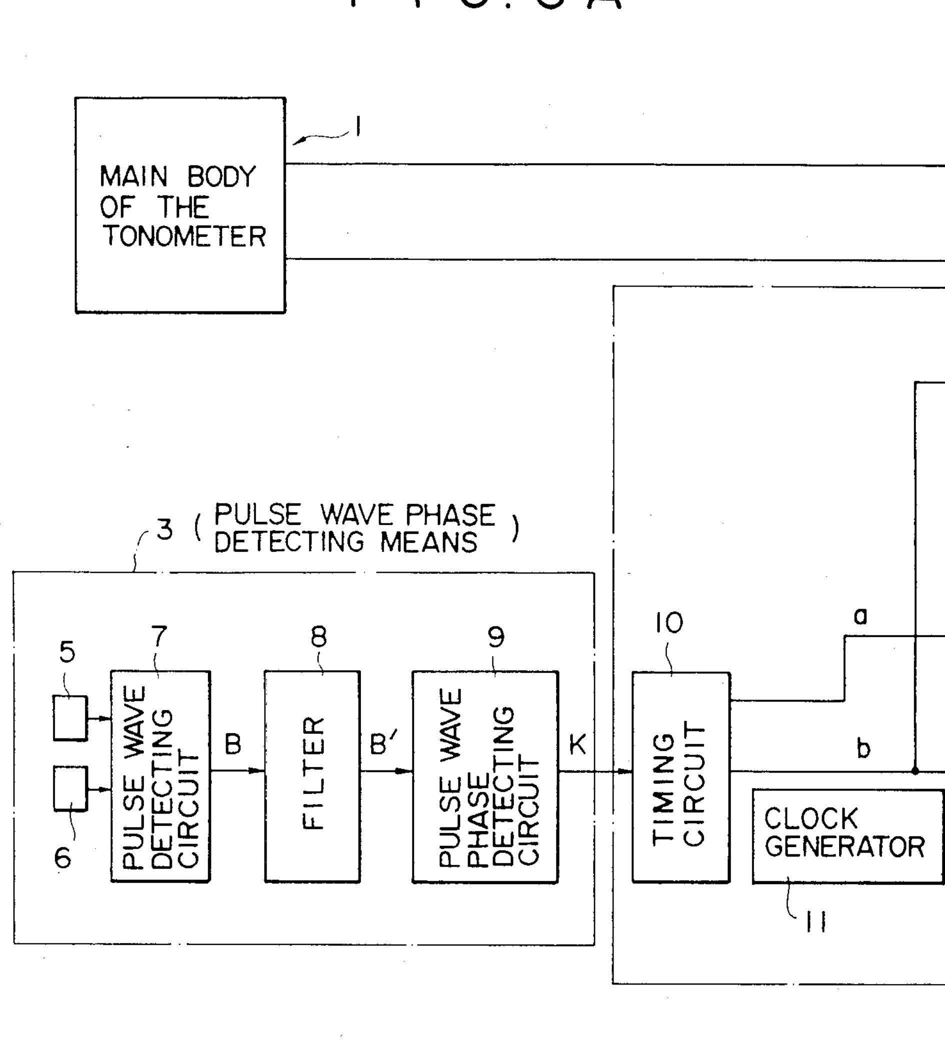
FIG. 6A and FIG. 6B taken together as in FIG. 6, are illustrations of a circuit diagram for explaining a second embodiment of a tonometer according to the present invention.
Figure 6:
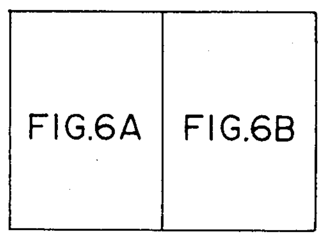
Figure 6B:
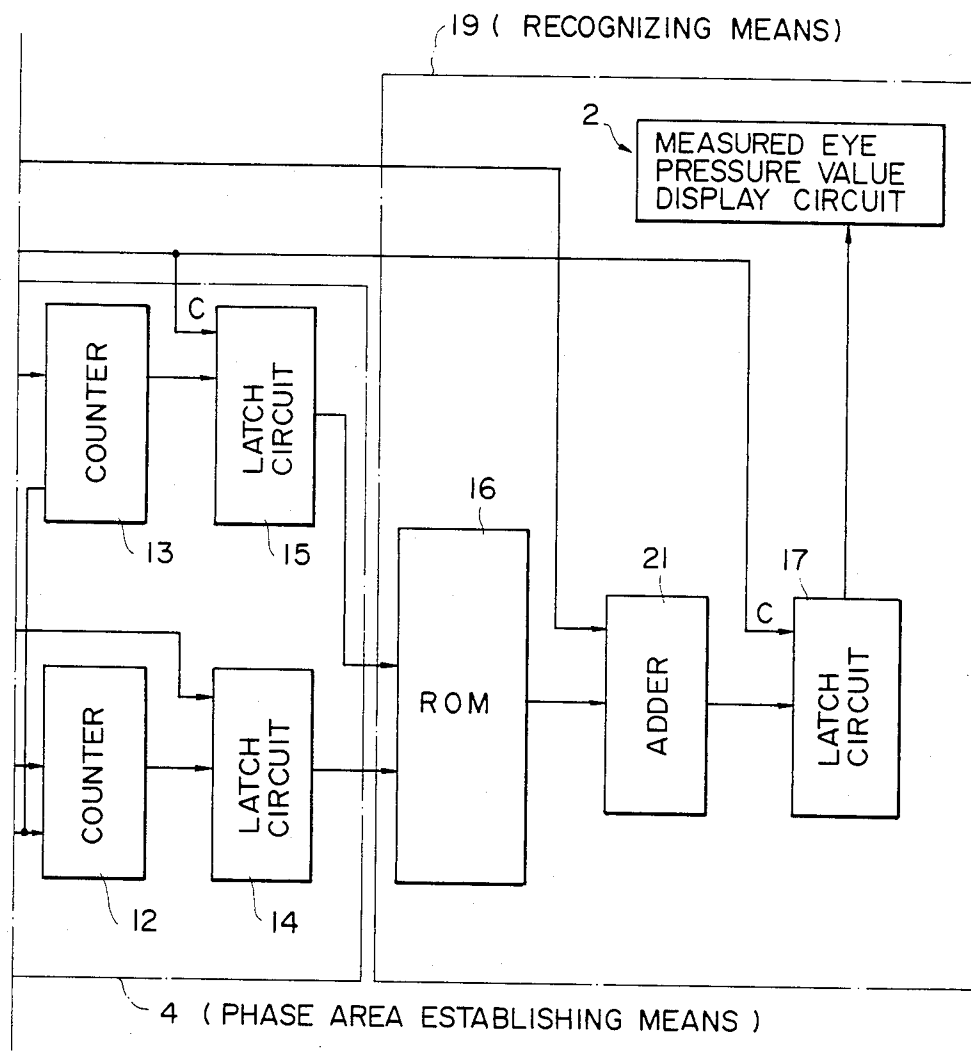

FIGS. 6A and 6B illustrate a second embodiment of a tonometer according to the present invention. The tonometer of this second embodiment comprises a ROM 16, as a memory means, for memorizing an eye pressure corrected value corresponding the recognizing means to the phase area, and adder, as a correcting means, for correcting the measured eye pressure value according to the output of the ROM 16, and a measured eye pressure value display circuit 2, as a display means, for displaying the corrected measured eye pressure value according to the output of the adder 21 in order to recognize the measured eye pressure value corresponding to the phase area of the eye pressure measuring time.

According to this second embodiment, the examiner is able to directly recognize the measured eye pressure value obtained by removing an error due to eye pressure fluctuation caused by pulse wave fluctuation.

In the above-described embodiments, if the capacity of the ROM 16 and the bit number of the counters 12 and 13 and the latch circuits 14 and 15 are increased, the phase area of the pulse wave A can be more finely divided, thereby to improve the reliability on the measured eye pressure value. Moreover, the tonometer according to the present invention is also applicable to one, in which a printer is used instead of the measured eye pressure value display circuit 2 for printing out the measured eye pressure value.

What is claimed is:

1. A tonometer comprising eye pressure measuring means including fluid discharging means for discharging a fluid toward an eye to be tested;

pulse wave phase detecting means for detecting a phase cycle of pulse wave due to pulse fluctuation of the eye to be tested;

pulse wave phase area establishing means for establishing whether or not an eye pressure measurement was carried out in any phase area of said pulse wave, according to an output pulse caused by a fluid discharge during the eye pressure measurement and an output of said pulse wave phase detecting means;

recognizing means for recognizing a measured eye pressure value corresponding to a phase area of the eye pressure measuring time according to the output of said pulse wave phase area establishing means.

2. The tonometer as claimed in claim 1, wherein said recognizing means includes memorizing means for memorizing a phase area information of the pulse wave, and display means for displaying whether or not the eye pressure measurement was carried out in any phase area, according to the output of said memorizing means in order to recognize a measured eye pressure value corresponding to a phase area of the eye pressure measuring time.

3. The tonometer as claimed in claim 1, wherein said recognizing means includes memorizing means for memorizing an eye pressure corrected value corresponding to said phase area, correcting means for correcting said measured eye pressure value according to an output of said memorizing means, and measured eye pressure value display means for displaying a corrected measured eye pressure value in order to recognize a measured eye pressrue value corresponding to a phase area of the eye pressure measuring time according to an output of said corresponding means.

4. The tononmeter as claimed in claim 1, wherein said pulse wave phase detecting means includes a pulse detecting circuit for outputting a pulse signal corresponding to pulse fluctuation of the subject to be tested, and a pulse phase detecting circuit for outputting a rectangular wave according to a pulse signal output from said pulse detecting circuit.

5. The tonometer as claimed in claim 1, wherein said pulse detecting circuit and said pulse phase detecting circuit are provided with a filter adapted to remove a noise and disposed therebetween.

6. The tonometer as claimed in claim 4, wherein said phase area establishing means includes a timing circuit for outputting a reset signal during the rising time of a rectangular wave output from said pulse phase detecting circuit, clock generator for generating a clock pulse, counter means for counting a clock pulse output from said clock generator so that the count is reset by a reset signal output from said timing circuit, a first latch circuit for outputting a count number during the reset time everytime when said counter means is reset, and a second latch circuit for outputting a count number of said count means during the outputting time of an output pulse according to fluid discharge during the eye pressure measuring time.

* * * * *

UNITED STATES PATENT AND TRADEMARK OFFICE
CERTIFICATE OF CORRECTION

PATENT NO. : 4,799,489

DATED : January 24, 1989

INVENTOR(S) : MASAYUKI HIDESHIMA

It is certified that error appears in the above-identified patent and that said Letters Patent is hereby corrected as shown below:

Claim 3, line 9, change "pressrue" to -- pressure --; and line 11, change "corresponding" to -- correcting --.

Signed and Sealed this

Fourth Day of July, 1989

*Attest:*

DONALD J. QUIGG

*Attesting Officer*

*Commissioner of Patents and Trademarks*

UNITED STATES PATENT AND TRADEMARK OFFICE

CERTIFICATE OF CORRECTION

PATENT NO. : 4,799,489

DATED : January 24, 1989

INVENTOR(S) : Masayuki HIDESHIMA

It is certified that error appears in the above-identified patent and that said Letters Patent is hereby corrected as shown below:

Claim 1, line 33, after "means;" insert --and--.

Claim 3, line 14, change "pressrue" to --pressure--.

Claim 3, line 16, change "corresponding" to --correcting--.

Claim 5, line 24, change "1" to --4--.

Signed and Sealed this

Twelfth Day of December, 1989

*Attest:*

JEFFREY M. SAMUELS

*Attesting Officer* *Acting Commissioner of Patents and Trademarks*